United States Patent
Atmanspacher

(10) Patent No.: US 9,506,172 B2
(45) Date of Patent: Nov. 29, 2016

(54) COMPRESSIVE CIRCULAR KNIT FOR PULLING OVER AN ARTICULATED EXTREMITY

(71) Applicant: medi GmbH & Co. KG, Bayreuth (DE)

(72) Inventor: Jan Atmanspacher, Warmensteinach (DE)

(73) Assignee: MEDI GMBH & CO. KG, Bayreuth (DE)

( * ) Notice: Subject to any disclaimer, the term of this patent is extended or adjusted under 35 U.S.C. 154(b) by 463 days.

(21) Appl. No.: 14/255,601

(22) Filed: Apr. 17, 2014

(65) Prior Publication Data

US 2014/0316312 A1    Oct. 23, 2014

(30) Foreign Application Priority Data

Apr. 18, 2013   (DE) .................... 10 2013 103 914

(51) Int. Cl.
| | |
|---|---|
| *D04B 1/26* | (2006.01) |
| *A61F 13/08* | (2006.01) |
| *D04B 1/22* | (2006.01) |
| *A61H 1/00* | (2006.01) |

(Continued)

(52) U.S. Cl.
CPC ............... *D04B 1/265* (2013.01); *A61F 13/08* (2013.01); *A61H 1/008* (2013.01); *D04B 1/22* (2013.01); *D04B 1/26* (2013.01); *A61F 13/061* (2013.01); *A61F 13/101* (2013.01); *D10B 2509/028* (2013.01)

(58) Field of Classification Search
CPC .......... D04B 1/26; D04B 1/265; D04B 7/18; D04B 9/52; D04B 11/28; D04B 21/207; A61F 13/08; A61F 13/061; A61F 13/101
See application file for complete search history.

(56) References Cited

U.S. PATENT DOCUMENTS

| | | | | |
|---|---|---|---|---|
| 663,749 | A * | 12/1900 | Gorse ..................... | A61F 13/00 2/62 |
| 4,269,181 | A * | 5/1981 | Delannoy ......... | A61F 13/00021 602/58 |
| 4,674,489 | A * | 6/1987 | Lundy ..................... | D04B 1/18 602/76 |

(Continued)

FOREIGN PATENT DOCUMENTS

| | | |
|---|---|---|
| DE | 10 2008 021 998 A1 | 11/2009 |
| DE | 10 2008 059 241 A1 | 6/2010 |

(Continued)

*Primary Examiner* — Danny Worrell
(74) *Attorney, Agent, or Firm* — Lucas & Mercanti, LLP

(57) ABSTRACT

A compressive circular knit for pulling over an articulated extremity, consisting of a knitting thread and an elastic thread, which form the loops, and an inlaid elastic weft thread, comprising two first knitted fabric portions which are spaced apart from each other in the knitted fabric longitudinal direction and which are knitted with floating and there is provided a knitted fabric region consisting of further different knitted fabric portions adjoining each other in the circumferential direction, wherein the knitted fabric region consists of: a second knitted fabric portion (4) knitted with floating, wherein the float count is greater than that of a first knitted fabric portion (2), two third knitted fabric portions (5) adjoining the second knitted fabric portion (4) in the circumferential direction which are each knitted with floating, wherein the floats of any one course are knitted offset relative to the next course, and also a fourth knitted fabric portion (7) provided in the circumferential direction between the two third knitted fabric portions (5) and knitted plain.

15 Claims, 3 Drawing Sheets

Figure 1:
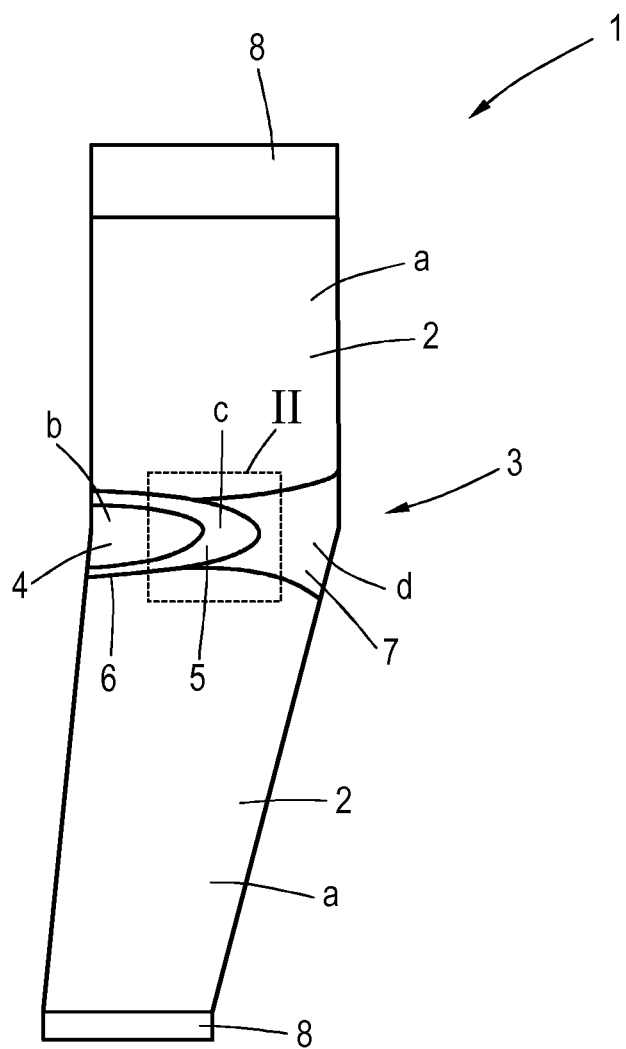

(51) Int. Cl.
*A61F 13/06* (2006.01)
*A61F 13/10* (2006.01)

(56) References Cited

U.S. PATENT DOCUMENTS

| | | | | |
|---|---|---|---|---|
| 5,419,161 | A * | 5/1995 | Bodenschatz | A61F 13/061 2/16 |
| 6,725,691 | B2 * | 4/2004 | Yakopson | A61F 13/08 2/240 |
| 9,358,172 | B2 * | 6/2016 | Collins | D04B 1/18 |
| 2009/0275873 | A1 * | 11/2009 | Achtelstetter | A61F 13/08 602/76 |
| 2012/0289875 | A1 | 11/2012 | Matsuo | |
| 2014/0316312 | A1 * | 10/2014 | Atmanspacher | D04B 1/265 601/84 |

FOREIGN PATENT DOCUMENTS

| | | |
|---|---|---|
| FR | 2 781 816 A1 | 2/2000 |
| FR | 2 801 495 A1 | 6/2001 |
| WO | 2008/069522 A1 | 6/2008 |

\* cited by examiner

COMPRESSIVE CIRCULAR KNIT FOR PULLING OVER AN ARTICULATED EXTREMITY

CROSS-REFERENCE TO RELATED APPLICATIONS

This application claims the priority of DE 10 2013 103 914.6 filed Apr. 18, 2013, which is incorporated by reference herein.

The invention relates to a compressive circular knit for pulling over an articulated extremity, consisting of a knitting thread and an elastic thread, which form the loops, and an inlaid elastic weft thread.

Compressive circular knits of this type are frequently used as a medical aid in compression therapy. They serve to create pressure from the outside on the tissue of the enclosed extremity in order that the lymphatic or venous system may be relieved. Compression knits of this type are constructed as a circular knit to avoid a longitudinal seam. They consist of a plurality of different threads in that a knitting thread and an elastic thread serve to form the knitted loop stitches, the elastic thread endowing the knit with in-principle extensibility. To exert the required pressure on the extremity, an elastic weft thread is laid in to pass through the courses. The weft thread lies between loop head and loop foot.

The compressive circular knit is frequently worn on the arm or on the leg in the region of the elbow or knee joint, i.e., in a region where movement takes place and/or the particular joint opens and closes. Compression knits of the type in question which are used here are constructed as simple circular knits in tubular form. Owing to the movement of the extremity, however, the wearing comfort is occasionally compromised, since the material will kink up in the region of the joint inside surface and become overextended in the region of the joint outside surface as the joint closes.

The problem addressed by the invention is therefore that of specifying a compressive circular knit that offers improved wearing comfort.

To solve the problem, the invention provides a compressive circular knit for pulling over an articulated extremity, consisting of a knitting thread and an elastic thread, which form the loops, and an inlaid elastic weft thread, comprising:
two first knitted fabric portions which are spaced apart from each other in the knitted fabric longitudinal direction and which are knitted with floating and wherebetween there is provided a knitted fabric region consisting of further different knitted fabric portions adjoining each other in the circumferential direction,
wherein the knitted fabric region consists of:
a second knitted fabric portion knitted with floating, wherein the float count is greater than that of a first knitted fabric portion,
two third knitted fabric portions adjoining the second knitted fabric portion in the circumferential direction which are each knitted with floating, wherein the floats of any one course are knitted offset relative to the next course,
and also a fourth knitted fabric portion provided in the circumferential direction between the two third knitted fabric portions and knitted plain.

The compressive circular knit of the present invention comprises various separate and mutually different knitted fabric portions which, owing to their special structure, endow the circular knit of the present invention with an anatomical shape that approximates the anatomy of the extremity. The circular knit of the present invention can in this way be constructed to be slightly angled; that is, it is possible to produce a slightly bent or angular shape which is an inherent property of the unstressed knit, so this shape—combined with special haptic properties resulting from the differing knitting of the individual knitted fabric portions—engenders distinctly improved wearing comfort particularly in the problematic zones in the region of the joint inside and outside surfaces.

Two first knitted fabric portions are firstly provided for this in the circular knit which are spaced apart from each other in the knitted fabric longitudinal direction. They are knitted with a float; that is, not every needle produces a knitted loop stitch and, instead, a needle will miss out a knitted loop stitch in a defined rhythm depending on the type of float chosen. These two first knitted fabric portions constitute the essential, areally largest regions of the circular knit. The present invention then provides therebetween a knitted fabric region which in the donned position locates in the region of the joint. This knitted region, which describes a full peripheral orbit of the circular knit and, viewed in the knitted fabric longitudinal direction, extends over a region of several centimeters, consists of altogether three further, separate and differently knitted fabric regions.

There is provided a second knitted fabric region which—like the first knitted fabric region—is likewise knitted with floating. However, the second knitted fabric region is knitted such that the float count is greater than the float count in the first knitted fabric portion. Whereas, for example, in the case of a 1:3 float in the first knitted fabric portion only every fourth needle misses out a knitted loop stitch (and hence therefore the knitted thread and the elastic thread float), a 1:1 float in the second knitted fabric region for example means that every second knitted loop stitch is missed out, so there are accordingly a large number of floating knitted thread portions. In this way, a considerable volume of thread material which is floating, i.e., not intermeshingly bound, is realized. The result of this then is that this floating thread material will kink up in a quasi plush-like manner when the inlaid weft thread, which confers the compressive properties, contracts, which in the region of every float will cause the untethered thread material there to likewise contract and kink up slightly in the process. Since there is a large float count, associated with a large number of courses, the floating knitted thread will consequently kink up over a large area, resulting in a raised fabric structure having plush-like haptics and a soft hand. Owing to the slight contraction of the weft thread in the circumferential direction, the overall effect further includes the fact that, viewed in the knitted fabric longitudinal direction, the adjoining first knitted fabric portions are slightly pulled toward each other, so a slight bend/angle becomes established in this region, relative to the knitted fabric longitudinal direction. The float stitches and the knitted loop stitches preferably extend uniformly in the direction of the wales, resulting in rows of float stitches and adjacent knitted loop stitches, which alternate in the case of a 1:1 float.

This second knitted fabric portion becomes positioned in the region of the joint inside surface when the compressive circular knit of the present invention is donned. This region is generally quite sheltered and the skin accordingly sensitive, so the plush-like surface there serves to confer some cushioning and/or a haptically pleasant wearing comfort.

The invention further provides two third knitted fabric portions which adjoin the second knitted fabric portion in the circumferential direction and which in turn are knitted differently. They likewise comprise a knitted float wherein, according to the present invention, the floats of any one course are knitted offset relative to the next course. This means that, for example, when a float of a first row of loops is formed by knitting at a first needle, the float in the adjacent second row will be formed not at the same needle but, for example, at the directly adjacent needle, so a float offset by, for example, one needle is obtained from course to course. This produces a surface structure which endows the knit with a certain stability which in turn leads to a reduction in creasing; that is, the knitted fabric is quasi made somewhat firmer in this region as a result of the float offset. The offset floats in turn lead to a corresponding surface structure since here too the weft thread will cause slight contraction of the particular float. This accordingly results in the formation of quasi line-shaped elevations, which have a stabilizing effect and work to oppose creasing. The two third knitted fabric portions adjoin the second knitted fabric portion sideways in the circumferential direction, enclosing said second portion in the circumferential direction.

Finally, a fourth knitted fabric portion is provided between the two third knitted fabric portions to conclude the knitted fabric region. This fourth knitted fabric portion is simply plain knit. Every needle here produces a loop, resulting in a very high loop count. The loop count is greater than the loop count in the adjoining first knitted fabric portions which, as described, are knitted with floating. Due to the higher loop count, this leads to higher knitted bulk in the fourth knitted fabric portion, which gives rise in turn to a geometric effect. This is because an outwardly directed bend and/or an outwardly directed elongation can thereby be produced in the region of this knitted fabric side to be positioned on the joint outside surface.

Altogether, therefore, four differently knitted fabric regions are provided in the circular knit of the present invention, viz., the two first knitted fabric regions knitted with floating; the second knitted fabric region which forms the plush-like surface and which is knitted with, compared with the first knitted fabric portion, lower loop count but higher float count; the two third knitted fabric portions which are knitted with floats offset from row to row and which serve to provide stabilization in the circumferential direction; and the fourth knitted fabric portion which is plain knit and has a very high loop count without floating. Therefore, a knitted type of bend is formed in the region of each of the second and fourth knitted fabric portions as a result of the particular design of the knitted fabric region orbiting the circumference, in the second knitted fabric region as a result of the contraction of the weft thread due to the high float count and in the fourth knitted fabric region as a result of an elongation due to the very high loop count, i.e., the plain knit pattern.

The overall result produced in this way is a realization of an anatomically shaped knit which comprises a haptically pleasant imitated plush zone and which offers a very high wearing comfort but at the same time retains its compressive properties.

In a further development of the invention, the second knitted fabric portion may be knitted in an oval and/or ellipsoidal shape. This shape has transpired to be advantageous for the actual anatomy in the joint inside region, whether it is the elbow joint or whether it is the knee joint. But in principle it would of course also be conceivable to make the region rectangular, for example, yet the oval/ ellipsoidal shape has been found preferable.

As described, the two third knitted fabric portions adjoin the second knitted fabric portion on both sides in the circumferential direction. It is conceivable here for the two third knitted fabric portions to border the second knitted fabric portion laterally only, so the second knitted fabric portion directly adjoins the two first knitted fabric portions, viewed in the knitted fabric longitudinal direction. In an advantageous embodiment, however, the third knitted fabric portions completely surround the second knitted fabric portion, i.e., the second knitted fabric portion is enclosed by the third knitted fabric portions (which then, viewed peripherally, cohere in this respect). This is advantageous with regard to the crease reduction sought via the third knitted fabric portions.

As noted, the first knitted fabric portions are knitted with floating, preferably with an x:y float where x is <y. That is, at least a 1:2 float, preferably a 1:3 float is knitted, although a 1:4 float or a 2:5 float is equally realizable. Preferably, a 1:3 float is knitted.

As noted at the beginning, the second knitted fabric portion is also knitted with a float. An a:b float, where a is ≤b and b is <y, is preferred here. It is thus possible to knit here for example with a 1:1 float, resulting in a high float count. It is also possible for example to knit a 1:2 float as long as b is ensured to be <y and so, accordingly, the float count in this knitted fabric portion is greater than in the first knitted fabric portion. Preferably, however, a 1:1 float is knitted.

As noted, the third knitted fabric regions—whether they are completely separated or whether they cohere (enclosing the second knitted fabric region)—serve to stabilize the knit. For this the invention provides for the float offset from course to course. The float can be offset in each case by one loop or by two loops, in which case, however, an offset by one loop in each case is preferred. This means that in the case of a 1:3 float being also knitted here for example, the float shifts by one loop each time from course to course. This results in the formation of a slightly elevated linear structure as a result of the fact that the elastic weft thread would again somewhat contract the particular float. It is possible, then, to form elevated "lines" which monotonously extend in one direction. However, it is preferable to produce a zigzag pattern as a result of the float being offset for example via three or four adjacent courses, viewed circumferentially, in one direction, whereafter the offset direction reverses and the float is offset in the other direction via the next three or four courses. This then results in the formation of an elevated linear structure extending in a zigzag shape.

The knitting thread itself can be formed from a manufactured fiber, in particular PA, PES, PP, or from a natural fiber, in particular cotton or silk, in which case it is preferable to use a PA thread. It is conceivable in this connection to use knitting threads of differing color to form the first to fourth knitted fabric portions. This makes it possible to fabricate a multicolored circular knit wherein the different knitted regions, which differ in structure in the case of a unitary knitting thread color, are now also additionally distinguishable by the different colors. Usage of differingly colored knitting threads thus makes it possible to produce very differingly colored knits, which is visually very appealing in some instances.

The elastic thread advantageously has an elastane core wrapped with a thread formed from a manufactured fiber, in particular PA, PES, PP, or from a natural fiber, in particular cotton or silk. Preference is given to using a wrapper thread made of the same material as the knitting thread. Again the preference here is for the use of PA.

The weft thread finally is formed from an elastomer, preferably a PU-based elastomer.

In a further possible embodiment, elastic cuffs are knitted or sewn to the end regions of the first knitted fabric portions. As desired or required, therefore, the cuff itself can be produced during the production of the circular knit; alternatively, a prefabricated elastic cuff can also be attached by sewing.

The compressive circular knit according to the invention is preferably constructed as arm stocking for pulling over the region of the elbow joint. Alternatively, it can also be constructed as leg stocking, including in the form of pantyhose, for pulling over the region of the knee joint. The skin in the inside region of both the elbow joint and the knee joint is relatively sensitive, since it is scarcely used, which is why the cushioning to be disposed there according to the present invention, as realized via the second knitted fabric portion, has a particularly enhancing effect on the wearing comfort. Since the elbow joint in particular has a very large bending angle of far above 90°, in some instances even far above 120°, but the knee joint can in some instances also bend to a considerable extent, there is an advantage for the wearing comfort in the formation of the fourth knitted fabric portion also and for a high level of wearing comfort in the overall result of the slightly bent basic shape of the circular knit.

Figure 2:
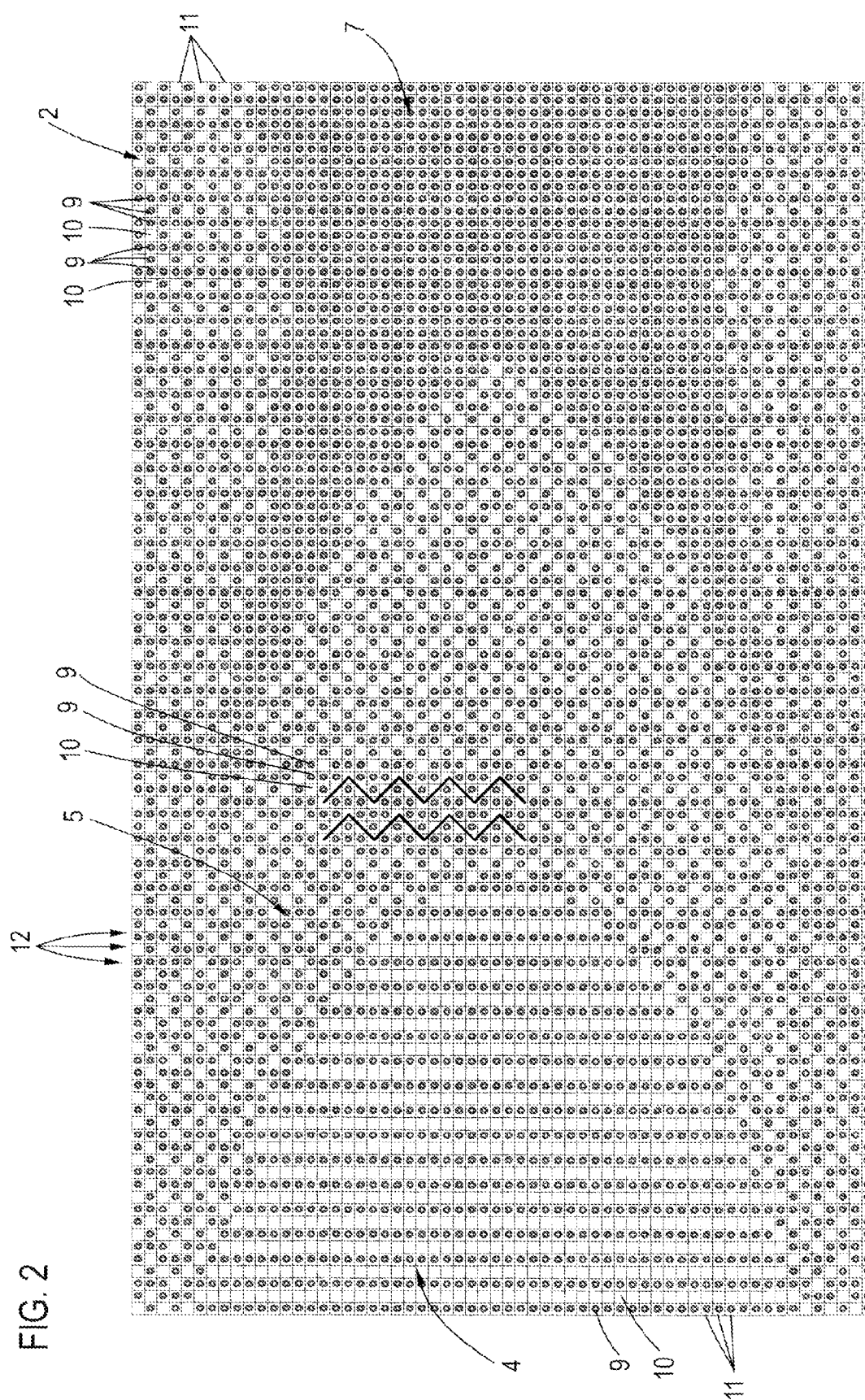
Figure 3:
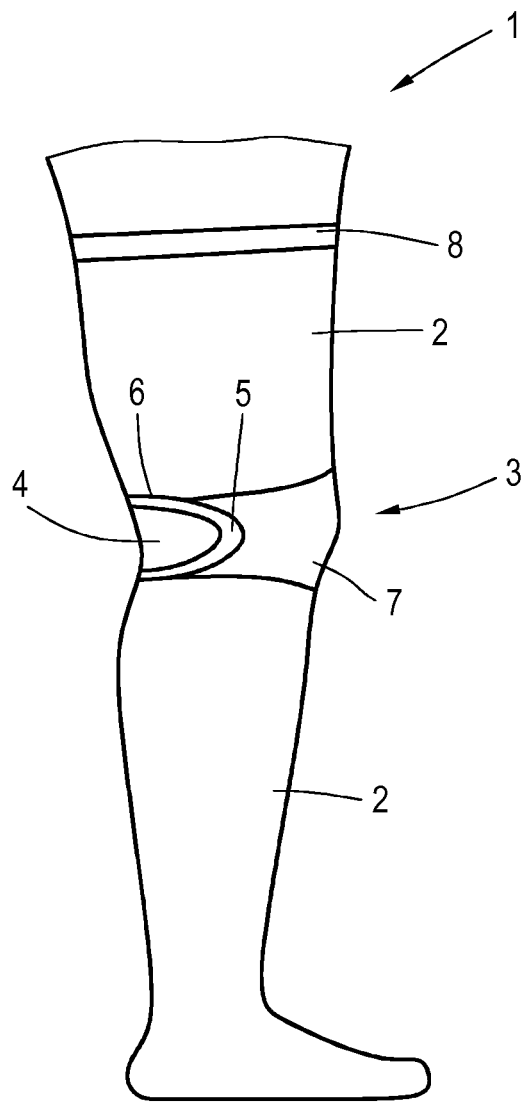

Further advantages, features and details of the invention will become apparent from the working example described hereinbelow and also from the drawings, where FIG. 1 shows an in-principle depiction of an inventive circular knit of a first embodiment, FIG. 2 shows a knitting pattern for depicting the various ways to knit the various knitted fabric portions, and FIG. 3 shows an in-principle depiction of an inventive circular knit of a second embodiment.

FIG. 1 shows an inventive compressive circular knit 1 formed from altogether three threads. Firstly, from a knitting thread and an elastic thread for loop formation wherein the knitting thread used is preferably a PA thread and the elastic thread used is a thread having an elastane core and a PA thread wrapper. An inlaid elastic weft thread is further used to form the knit. The circular knit is fabricated on a circular knitting machine such that the weft thread becomes laid into the knit such that it extends between the loop feet and the loop heads of two knitted rows.

The inventive circular knit 1 shown in FIG. 1 is constructed as an arm stocking to be worn over the upper and lower arm, i.e., to cover the elbow joint, and consists of a plurality of separate knitted fabric portions. There are first of all two first knitted fabric portions 2 which, based on FIG. 1, form the upper and lower knitted fabric regions and in terms of area are the largest knitted fabric portions. The two first knitted fabric portions 2 are knitted with floating, preferably with a 1:3 float, meaning that, within any one course, three loops are plain knitted, while the subsequent loop is missed and the knitting thread and the elastic thread are floating there. The weft thread is inlaid and/or co-extensive.

Between the two first knitted fabric portions 2 there is provided a peripherally completely orbiting knitted fabric region 3, which consists of three further separate and differently knitted fabric portions. There is firstly provided a second knitted fabric portion 4, which preferably has an oval shape. It is likewise knitted with floating, but differs in the knit from the first knitted fabric portions 2 in that the float count in the second knitted fabric portion 4 is distinctly higher than in the first knitted fabric portions 2. It is preferable to knit with a 1:1 float, meaning a plain knit loop and a float alternate in each case. Since the weft thread is also laid in here, the resiling force, i.e., the contraction of the weft thread, will cause the knitting thread and the elastic thread within a float to likewise be contracted and/or kinked up. Since the second knitted fabric portion has a very high float count, therefore giving a high untethered volume of knitted fabric thread and elastic thread, and preferably a 1:1 float, the consequential result is a high, vaulted-up volume of thread, which endows this knitted fabric portion 4 with a prominent, raised structure having a plush-like hand. The knitted fabric portion 4 is knitted, as will be appreciated, such that this raised cushioning is situated, in terms of the donned position of the circular knit 1, on the knitted fabric inside surface, and therefore comes to be in contact with the skin. Since the floats and loops in the second knitted fabric region are congruent from course to course, the consequential result is that, viewed in the knitted fabric longitudinal direction, there are a multiplicity of directly neighboring raised lines which are only separated by one loop and which, since they are only separated by one loop, are accordingly very close together, so the overall result obtained is a quasi uninterrupted raised plush-like surface. The loop count in the second knitted fabric portion 4 is accordingly distinctly lower than in the first knitted fabric portions 2, while by contrast the float count is distinctly higher than in the two first knitted fabric portions 2.

The knitted fabric region 3 further comprises two third knitted fabric portions 5 which—viewed in the circumferential direction—border onto the second knitted fabric portion 4 from both sides. In the working example shown, the two third knitted fabric portions 5 (only one of which is shown in FIG. 1, the other is situated on the opposite side of the knit) are connected to each other via corresponding connecting portions 6, which are knitted identically, to form a quasi uninterrupted knitted fabric portion which completely surrounds the second knitted fabric portion 4.

The third knitted fabric portions are also knitted with floating, preferably with a 1:2 float, but a 1:3 float is also conceivable. What is important here is that the individual floats of neighboring courses are offset relative to each other, preferably by one loop and/or needle, to form—again resulting from the fact that the weft thread contracts and/or slightly kinks up the particular float—line-shaped elevations which extend in a quasi oblique manner across the knit. Preferably, a zigzag pattern is knitted here in that the offset direction of the floats reverses, i.e., the floats are for example offset across three, four or five courses in one circumferential direction, whereafter the offsetting direction reverses and the floating is offset across the next three, four or five loop directions in the other circumferential direction, whereafter the offset reverses again, and so on. The result is accordingly a zigzag structure which has a stabilizing, i.e., fabric stiffening, effect and works to oppose creasing.

Finally, a fourth knitted fabric portion 7 provided in knitted fabric region 3 adjoins the third knitted fabric portions 5 and terminates the knitted fabric region 3. Within this knitted fabric portion 7, the fabric is plain knit, i.e., every needle knits a loop. The loop count is accordingly extremely high, i.e., maximal, here, and the maximum volume of thread is consequently also present, so a quasi elongate knitting portion is formed as viewed in the knitted-fabric longitudinal direction and makes it possible, see FIG. 1, to form a kind of bend or angular structure in this region. Since, as described, the second knitted fabric portion 4 is knitted with extremely high float count and the weft thread there causes powerful contraction of the knit, resulting in the plush-like kinking up of the knitting thread, a slight bend will likewise result in this region. Overall, therefore, the knitted fabric is engineered to contract on one side in the second knitted fabric portion 4 to produce, viewed geometrically, a bent shape so to speak, while on the opposite side, as the result of the extremely high loop count knitted, an elongation occurs which likewise leads to the formation of a bent shape, but in the opposite direction. The overall result is therefore, as shown in FIG. 1, a basically bent knitted fabric shape which slightly approximates the extremity in the extended state and which improves the wearing comfort linked to the fact that some cushioning, realized via the second knitted fabric portion 4, can be positioned on the sensitive inside surface of the joint.

At each end of a first knitted fabric portion 2 there is further provided a cuff 8 which can either be integrally knitted thereto, but which alternatively can also be separately prefabricated and attached thereto by sewing. The inside surface of the cuff can if necessary be covered with a slightly adherent anti-slip coating.

FIG. 2 shows a stitching diagram as detail (II) from the circular knit 1 of FIG. 1, parts of all knitted fabric portions 2, 4, 5 and 7 being shown in this stitching diagram.

FIG. 2 is a technical pattern depicted as an x-y matrix of x times y individual pixels. Each pixel corresponds to a potential loop which can be knitted as such or which can float. Each knitted loop is depicted as an "o" in the corresponding pixel. Pixels left blank indicate that the thread is floating there.

FIG. 2 firstly shows the two first knitted fabric portions 2, which are depicted in FIG. 2 in the region of the upper and lower edge, primarily at right. As is apparent from the stitching diagram, this knitted fabric portion, i.e., ultimately the base knit, is knitted with a 1:3 float. Plainly, a group of three knitted loops 9 is followed by a float 10, which in turn is followed by three knitted loops 9, which are in turn followed by a float 10, and so on. The individual courses 11 are plainly knitted in this region such that the particular float 10 is offset from course 11 to course 11 by two loops at a time.

FIG. 2 depicts the second knitted fabric region 4 in terms of its stitching diagram on the opposite side. This second knitting region 4, which via the specific patterning is knitted as a raised, imitated plush portion, is knitted as a 1:1 float, meaning that a loop 9 and a float 10 alternate each time. A 1:1 wale construction is thus realized. As FIG. 2 shows, the courses 11 which lie on top of each other are knitted identically; that is, viewed in the knitted fabric longitudinal direction, identical courses 11 lie on top of each other.

As noted, this manner of knitting causes the elastic weft thread which, as described, is inlaid between loop head and loop foot, to contract in the region of the particular float 10, causing the untethered thread material to likewise contract and kink up slightly. Since all the floats 10, see FIG. 2, are in a line, which of course also applies mutatis mutandis to loops 9, the result is that quasi line- and/or row-shaped elevations of thread are formed. Since these individual raised rows are only separated from each other by one loop 9 and/or one loop line, the logical result is a virtually uninterrupted, raised plush-like surface.

The second knitted fabric portion 4, as noted, is adjoined on both sides by the two third knitted fabric portions 5 which, when the connecting portions 6 have been knitted, can be connected to each other and can enclose the oval or ellipsoidal second knitted fabric portion 4, see FIG. 1. As is discernible from the knitting pattern in FIG. 2, the construction in the knitted fabric portion 5 is realized as a 1:2 float, meaning that two loops and one float are knitted here in a continuing pattern. The individual courses 11 are knitted such that the respective float 10 is offset from course 11 to course 11 by one loop/needle at a time, the direction of offset reversing after every third course 11. The floats 10 thus describe a zigzag pattern as drawn in FIG. 2 by way of example, see the two continuous lines. As FIG. 2 reveals, a multiplicity of such parallel zigzag lines are realized.

Again, the elastic weft thread slightly contracts in the region of each individual float 10, so the floating thread material is slightly kinked up. However, since the individual floats 10 are offset in the direction of the wales 12 (i.e., vertically to the courses 11) and are knitted in zigzag form, the result is that, in the final knit, the individual float-specific thread kink-ups altogether form a corresponding, somewhat raised zigzag row, in line with the float pattern. The zigzag rows, since they are knitted with a 1:2 float, are spaced apart from each other by two loops in the wale direction, as is shown by the loop diagram as per FIG. 2. These raised zigzag rows serve to stabilize the knitted fabric portions 5, which works to oppose creasing and/or the formation of creases. Although FIG. 2 shows a 1:2 float, it would also be conceivable here, of course, to knit a 1:3 float or a 2:4 float or a 2:5 float. It is merely important that the particular float be offset from row to row by one needle each time, forming the zigzag line structure.

Finally, FIG. 2 also shows the stitching diagram for the fourth knitted fabric portion 7. This knitted fabric portion 7 is plain knit, meaning that every needle knits a loop, as is unambiguously discernible from the stitching diagram. Thus, the loop count per unit area is highest here, so there is a high loop and thread volume there, which results in the formation in this region of a kind of elongation which results in the slight bent shape, see FIG. 1. By contrast, since the second knitted fabric portion 4 has the lowest loop count but the highest float count and, owing to the resilience of the elastic weft thread, a high contractible content, this region produces a slight contraction, so the slight bend is also formed on this side, see FIG. 1.

It must finally be noted, in addition, that the forms of knitting in the individual knitted fabric portions need not necessarily correspond to the pattern shown in FIG. 2. It is accordingly conceivable to knit the first knitted fabric portions 5, which are in principle knitted with an x:y float, where x is <y, not with the 1:3 float shown but instead also as a 1:4, 2:4 or 2:5 float. The second knitted fabric portion 4, knitted as a 1:1 float in the example, and knitted in principle with an a:b float, where a is ≤b and b is <y, can also be knitted for example as a 2:2 float or as a 1:2 float. It is always important, however, that the float count be higher than in the first knitted fabric portion 5. It preferable for the stitching diagram to be such that the unitary wales 12 shown in FIG. 2 be formed, resulting in the rowed or ribbed structure described.

The third knitted fabric portions 5 can also be knitted as a 1:3 float or as a 2:4 float, the important requirement being always the symmetrical offset of the float from course to course by one needle, so the zigzag structure is obtained.

Merely the fourth knitted fabric portion 7 should preferably always be knitted plain.

FIG. 3 finally shows a further embodiment of an inventive circular knit 1, here shown as a leg stocking. Said leg stocking consists ultimately of the same knitted fabric portions as the circular knit 1 in FIG. 1. There is thus again a base knit consisting of the first knitted fabric portions 2, while the lower first knitted fabric portion 2 shown in FIG. 3 also has a foot part which naturally, necessary, comprises a specific knit.

Between the two knitted fabric portions 2 there is again a knitted fabric region 3, which corresponds to that in FIG. 1.

Said knitted fabric region 3 here thus also consists of a second knitted fabric portion 4 which displays the imitated plush surface, i.e., the slightly raised, soft and smooth surface, which faces the leg or to be more precise the skin. The knitted fabric region 3 here is also completely enclosed by the third knitted fabric portions 5, which again are connected here to each other via the connecting portions 6. These are adjoined, to complete the knitted fabric region 3, by the fourth knitted fabric portion 7. The individual knitting patterns for the knitted fabric portions correspond to those described with regard to FIG. 1. Since what is concerned here is a leg stocking having an integrally knitted foot region, there is only one cuff 8 provided here.

Plainly, the knitted fabric region 3 here has also been constructed such that, in the donned position, the soft, cushioning second knitted fabric portion 4 faces with its plush-like, soft and raised surface toward the back of the knee and/or is disposed in the region of the back of the knee. The opposite region, elongated on account of the high loop count and formed by knitted fabric portion 7, covers the region of the knee. This circular knit can also be constructed as a leg stocking without foot region, but with a second cuff, or as a complete pair of pantyhose.

The invention claimed is:

1. A compressive circular knit for pulling over an articulated extremity, consisting of a knitting thread and an elastic thread, which form the loops, and an inlaid elastic weft thread, comprising:
   two first knitted fabric portions which are spaced apart from each other in the knitted fabric longitudinal direction and which are knitted with floating and wherebetween there is provided a knitted fabric region consisting of further different knitted fabric portions adjoining each other in the circumferential direction,
   wherein the knitted fabric region consists of:
      a second knitted fabric portion knitted with floating, wherein the float count is greater than that of a first knitted fabric portion,
      two third knitted fabric portions adjoining the second knitted fabric portion in the circumferential direction which are each knitted with floating, wherein the floats of any one course are knitted offset relative to the next course,
      and also a fourth knitted fabric portion provided in the circumferential direction between the two third knitted fabric portions and knitted plain.

2. The compressive circular knit according to claim 1, wherein the second knitted fabric portion is knitted in an oval shape.

3. The compressive circular knit according to claim 1, wherein the third knitted fabric portions completely surround the second knitted fabric portion.

4. The compressive circular knit according to claim 1, wherein the first knitted fabric portions are knitted with an x:y float, where $x<y$.

5. The compressive circular knit according to claim 4, wherein the first knitted fabric portions are knitted with a 1:3 float.

6. The compressive circular knit according to claim 4, wherein the second knitted fabric portion is knitted with an a:b float, where $a \leq b$ and $b<y$.

7. The compressive circular knit according to claim 6, wherein the second knitted fabric portion is knitted with a 1:1 float.

8. The compressive circular knit according to claim 1, wherein the third knitted fabric portions are knitted with respect to the float offset such that a zigzag pattern is obtained.

9. The compressive circular knit according to claim 1, wherein the third knitted fabric portions are knitted with a 1:2 float.

10. The compressive circular knit according to claim 1, wherein a knitting thread is formed from a manufactured fiber of PA, PES, PP, or from a natural fiber of cotton or silk.

11. The compressive circular knit according to claim 1, wherein knitting threads of differing color are used to form the first to fourth knitted fabric portions.

12. The compressive circular knit according to claim 1, wherein an elastic thread having an elastane core is wrapped with a thread formed from a manufactured fiber of PA, PES, PP, or from a natural fiber of cotton or silk, is used.

13. The compressive circular knit according to claim 1, wherein a weft thread formed from an elastomer is a PU-based elastomer.

14. The compressive circular knit according to claim 1, wherein elastic cuffs are knitted or sewn to the end regions of the first knitted fabric portions.

15. The compressive circular knit according to claim 1, wherein the knit is constructed as arm stocking for pulling over the region of the elbow joint or as leg stocking or pantyhose for pulling over the region of the knee joint.

\* \* \* \* \*